United States Patent
Anhäuser et al.

(10) Patent No.: US 6,278,036 B1
(45) Date of Patent: Aug. 21, 2001

(54) APPLICATION AID FOR FILM DRESSING

(75) Inventors: Dieter Anhäuser, Melsbach; Jürgen Ecker, Neuwied; Heike Schentek, Kurtscheid, all of (DE)

(73) Assignee: Lohmann GmbH & Co. KG, Neuwied (DE)

( * ) Notice: Subject to any disclaimer, the term of this patent is extended or adjusted under 35 U.S.C. 154(b) by 0 days.

(21) Appl. No.: 09/319,716
(22) PCT Filed: Nov. 21, 1997
(86) PCT No.: PCT/FF97/06528
 § 371 Date: Jul. 14, 1999
 § 102(e) Date: Jul. 14, 1999
(87) PCT Pub. No.: WO98/25559
 PCT Pub. Date: Jun. 18, 1998

(30) Foreign Application Priority Data

Dec. 11, 1996 (DE) .......................................... 296 21 366 U

(51) Int. Cl.⁷ ..................................................... A61F 13/00
(52) U.S. Cl. ................. 602/41; 602/42; 602/43; 602/44; 602/45; 602/46; 602/47
(58) Field of Search .................................................... 602/41

(56) References Cited

U.S. PATENT DOCUMENTS

| 4,619,253 | 10/1986 | Anhäuser et al. | 218/156 |
| 4,915,102 | 4/1990 | Alfred et al. | 128/156 |

FOREIGN PATENT DOCUMENTS

| 1 935 916A | 7/1969 | (DE) . |
| 33 44 334 C2 | 12/1983 | (DE) . |
| 0 066 899 B1 | 6/1982 | (EP) . |
| 0 120 570A | 3/1984 | (EP) . |
| 0 308 122A | 3/1989 | (EP) . |
| 0 473 918 B1 | 7/1996 | (EP) . |
| WO 89 07922A | 9/1989 | (WO) . |
| 2 297 260A | 7/1996 | (WO) . |

Primary Examiner—Michael A. Brown
Assistant Examiner—Lalita M. Hamilton
(74) Attorney, Agent, or Firm—Jordan and Hamburg LLP

(57) ABSTRACT

A film dressing, in particular for the human or animal body, consisting of a flexible, conformable polymer film which is detachably bonded on the side facing away from the skin to a supporting sheet and is provided on the side facing the skin with a pressure sensitive adhesive layer which is in turn provided with an at least two-part protecting layer which can be pulled off, is characterized in that the protecting layer has hinge-like connections at two opposite edges to the supporting sheet.

13 Claims, 2 Drawing Sheets

APPLICATION AID FOR FILM DRESSING

DESCRIPTION

Figure 1:
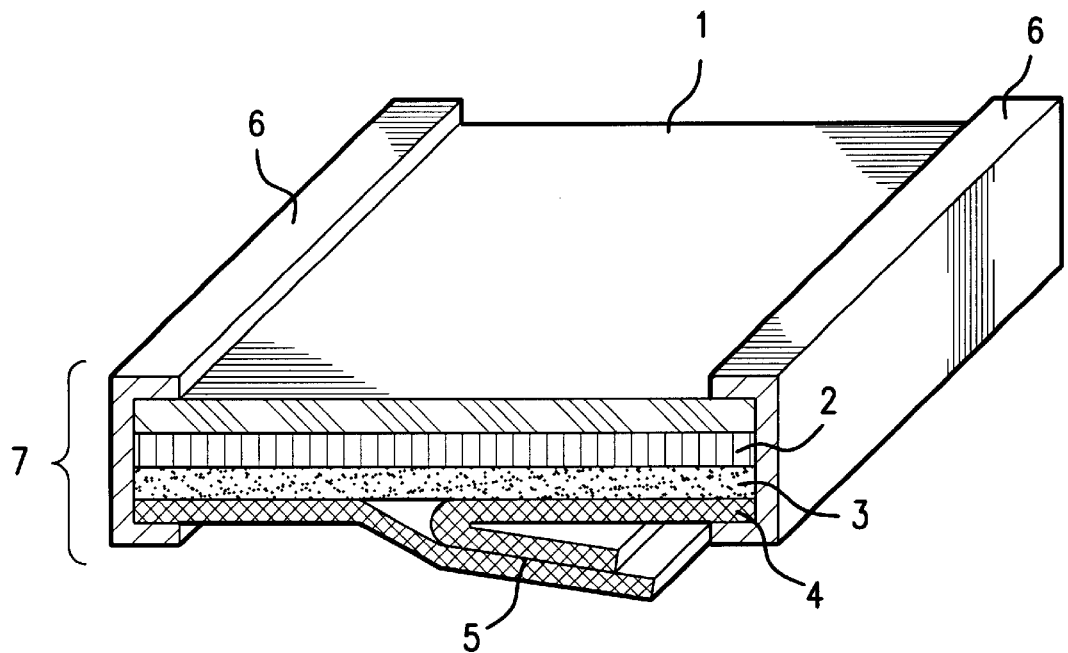

The invention relates to a film dressing, in particular for the human or animal body, consisting of a thin film which can be fastened by means of a pressure sensitive adhesive layer to the body. The dressing can be occlusive or nonocclusive.

Pressure sensitive adhesive, nonocclusive film dressings have been used for a long time in the medical sector. The term "nonocclusive" means in this connection that although the dressing is impermeable to bacteria and liquid water, it permits oxygen and water vapour to pass through. The last property in particular allows water vapour arising on the skin to escape through the dressing. The dressings are used, for example, for covering wounds and burns, as incision films, for dermal application of active ingredients or else for fixing medical instruments such as catheters or needles to the skin.

The transparent or opaque polymer films used in the dressings are continuous, that is to say they are not perforated and not microporous. The pressure sensitive adhesive layer which is applied must also be permeable to water vapour in such a way that the overall permeability of the dressing is not less than the required extent. In order to meet these requirements and provide a flexible, conformable dressing, the films must be extremely thin. However, this circumstance leads to great difficulties in applying the dressing. Thus, this often requires two people in order to prevent creasing of the films and self-adhesion of the adhesive areas.

Occlusive film dressings—dressings with a very low or no permeability for water vapour—are likewise indicated in certain cases. Extremely thin films are also used for these dressings, because of the required ability to conform, so that once again the same application difficulties arise as with nonocclusive dressings.

One contribution to solving the problem is disclosed in DE-A 19 35 916, wherein the area of the polymer film which is not coated with pressure sensitive adhesive is covered with a rigid supporting sheet which is pulled off only after application of the dressing. The remaining problems relate to the manipulation of the dressing on application and the pulling off of the protective sheet since it is absolutely necessary to avoid contamination of the pressure sensitive layer during this.

Approaches to solutions relate to designing the supporting sheet to have a larger area than the polymer film, which makes it possible to form grasping points free of pressure sensitive adhesive (DE-C 33 44 334), or attaching gripping strips near the edge of the supporting sheet (EP 0 066 899 and EP 0 473 918). These proposals suffer from being associated with the disadvantage of a considerable expenditure of material together with, in some cases, elaborate processing steps.

U.S. Pat. No. 4,915,102 describes another possibility in which the one-piece protecting layer, that is to say layer which can be detached again and which covers the pressure sensitive adhesive layer before application, has a hinge-like connection on one edge of the dressing to the supporting sheet. On application, the protecting layer which has been pulled off accordingly remains connected to the supporting sheet and is used eventually as grasping aid when pulling off the supporting sheet. However, only a relatively narrow, adhesive-free grasping rim is provided on the edge opposite to the hinge-like connection but is used for the application. As mentioned above, special industrial processing steps are needed to produce it.

It is therefore an object of the present invention to provide a film dressing which overcomes the known deficiencies in the convenience of use while being as simple as possible to produce.

This object is achieved, in the case of a film dressing consisting of a flexible, conformable polymer film which is detachably connected on the side facing away from the skin to a supporting sheet and is equipped on the side facing the skin with a pressure sensitive adhesive layer which in turn is provided with an at least two-part protecting layer which can be pulled off, by the protecting layer having hinge-like connections on two opposite edges to the supporting sheet.

This design permits, inter alia, the supporting sheet to have the same surface area as the polymer film, and thus additional cutting and/or punching processes to be avoided. The protecting layer parts can, after detachment from the pressure sensitive adhesive layer, be swung outwards and can be grasped for application of the dressing without the need to accept contamination of the pressure sensitive adhesive layer. After the polymer film has been pressed onto the skin, the supporting sheet can conveniently be pulled off with the attached parts of the protecting layer.

There are numerous possibilities for producing the hinge-like connection between protecting layer and supporting sheet, of which some of those particularly preferred will be described. On the one hand, the protecting layer can project in the form of a strip beyond the edge of the dressing and, after folding round this edge, is adhesively fastened to the supporting sheet surface facing away from the skin. A crease in the protecting layer promotes movability thereof around the hinge axis. The converse design, that is to say the supporting sheet is, after folding around the edge, fastened to the underside of the protecting layer, is also possible in principle but will remain restricted to special cases because of possible disadvantages.

In the case where circumstances allow the supporting sheet and the protecting layer to be produced from the same material, an integral flat material will be folded around the polymer film so that the ends come to rest on the side of the adhesive layer. The adhesion of the polymer film to this flat material is brought about by known methods.

In another preferred embodiment of the invention, the supporting sheet, polymer film coated with pressure sensitive adhesive and protecting layer have the same outer contours and the hinge-like connection between supporting sheet and protecting layer is formed by attaching a longitudinally creased strip, with one part adhering to the supporting sheet side facing away from the skin and the other part adhering to the free side of the protecting layer. The strip is preferably provided with pressure sensitive adhesive, but can also be fixed by other suitable adhesive systems. Sealing on at room temperature or with heat input provides further possibilities for fixing. It is, of course, unnecessary for the strip to enclose the entire length of the edge of the hinge; on the contrary, it is sufficient in some cases for only parts of the edge to be covered. All flexible sheet materials are suitable as material for the strip.

The film dressing according to the invention preferably has a quadrangular contour with the hinge-like connections being formed on opposite edges. The size of the polymer film need not correspond to the size of the supporting sheet; it may also be smaller so that the supporting sheet projects beyond the polymer film. In this case, the contour of the polymer film may differ from the supporting sheet. This applies, for example, when a polymer film with a rounded contour is covered by an angular—in particular quadrangular—protective sheet. If no straight edges are present in the case of a polymer film with a rounded contour, such as, for example, the circular shape, the contour of the supporting sheet will be chosen, for example, to have on opposite sides straight edges tangential to the rounded contour of the polymer film which have a length such that reliable hinge formation is ensured.

Known polymers are suitable as material for the supporting sheet, such as, for example, polyethylene, polypropylene, polyamide or polyester. However, textile flat materials and paper are also in use. The thickness of the supporting sheet varies between 20 $\mu$m and 200 $\mu$m, preferably 30–80 $\mu$m. Either the supporting sheet is bonded to the polymer film with a suitable adhesive, or the connection is brought about by the mechanical forces of adhesion which arise when the polymer film is produced by extrusion, casting or another known way of producing the film directly on the supporting sheet.

The polymer film is opaque or transparent and can be produced by known techniques from known raw materials. Examples of such raw materials are polyurethanes, polyvinyl chlorides, polyvinylidene chlorides, polyvinyl alcohols, polyacrylates, polysulphones, polystyrenes, polypropylenes, polyamides, ethylene/vinyl acetate copolymers, polyesters, polycarbonates, polyvinyl fluoride or other fluorine-containing polymers.

Polyurethanes are preferred to form a nonocculusive polymer film, and polyvinylidene chloride is preferred for an occlusive polymer film. The thicknesses of suitable polymer films are in the range 7 $\mu$m–120 $\mu$m, but preferably 15–50 $\mu$m. In the case of the nonocculusive polymer films, the permeability to water vapour should be at least 300 g×m−2×24 h−1.

The known physiologically acceptable pressure sensitive adhesive materials are suitable for constructing the pressure sensitive adhesive layer. Examples which may be mentioned are rubber, rubber-like synthetic homopolymers, copolymers or block polymers, polyacrylates and their copolymers, polyurethanes and silicones. The application rate of the pressure sensitive adhesive is 15–80 g/m2, preferably 30–50 g/m2.

The material for the protecting layer may be that also used for the supporting layer. However, it is additionally possible to employ, for example, polytetrafluoroethylene, cellophane, polyvinyl chloride, abhesively treated papers, metal foils and polymer-coated metal foils. The weights per unit area are 30–250 g/m2, preferably 50–150 g/m2. The side of the protecting layer in contact with the pressure sensitive adhesive layer must allow redetachment with a force which is less than that for detaching the supporting sheet from the polymer film. The ends of the at least two-part protecting layer which come to rest on the pressure sensitive adhesive layer are advantageously equipped in the usual way with grasping aids.

The pressure sensitive adhesive layer may contain active substances and thus allow dermal administration thereof. The present invention is therefore particularly used as transdermal therapeutic system characterized by extremely great adaptability to the skin, together with excellent wearing comfort. It is, of course, also possible to apply active substance-containing material to part of the pressure sensitive adhesive layer on the side facing the skin.

It is furthermore possible to apply to part of the pressure sensitive adhesive layer on the side facing the skin liquid-absorbing flat materials so that the dressing can be employed for wound management.

The invention is explained further by means of examples in figures. They are not depicted true to scale, and the thickness of the layers present is exaggerated for more clarity. Identical elements have the same reference numbers.

Figure 2:
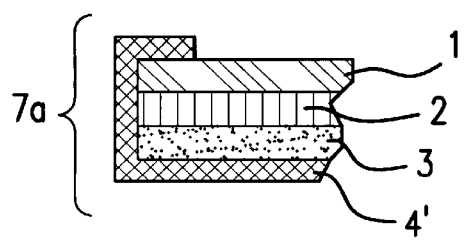
Figure 3:
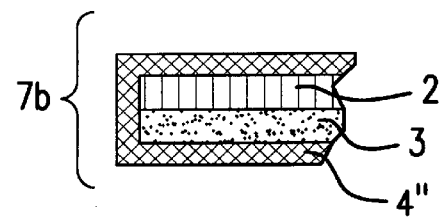
Figure 4:
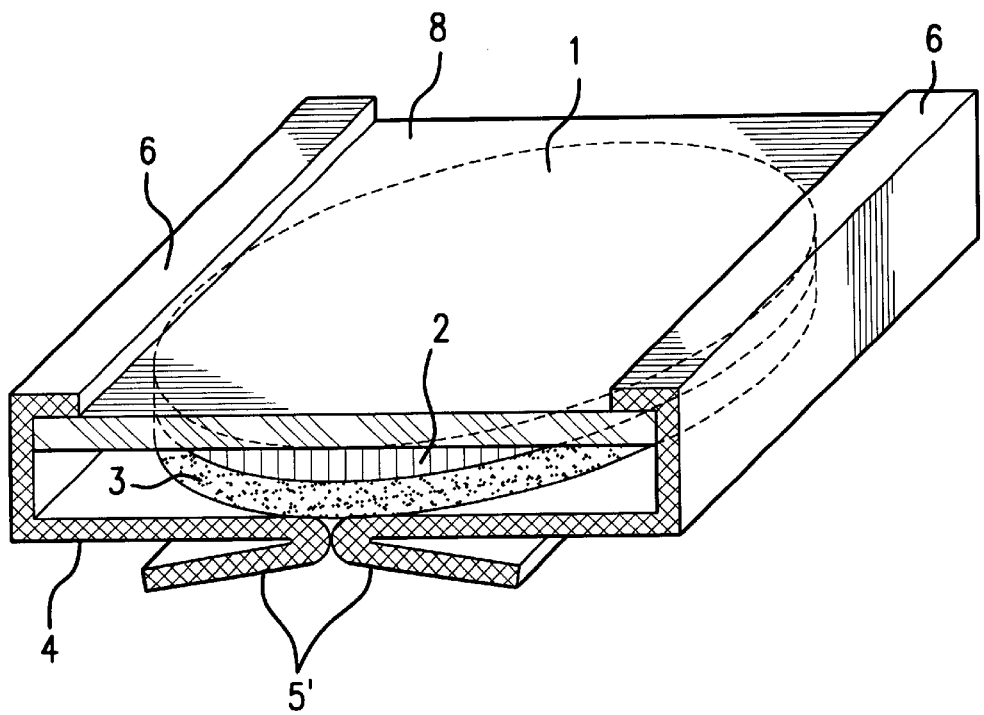
Figure 5:
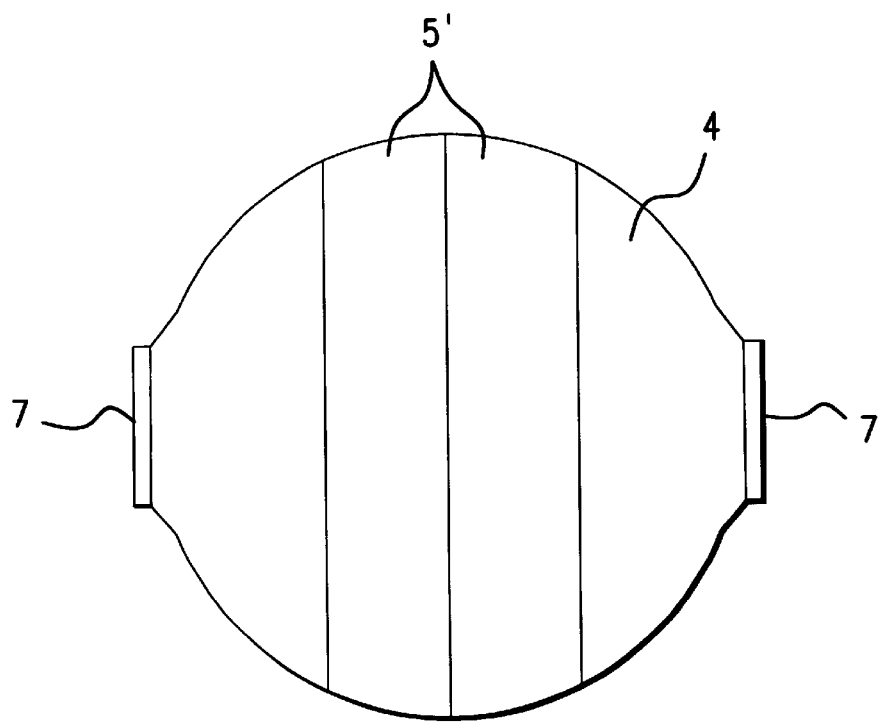

These show:

FIG. 1 a perspective view of a film dressing according to the invention,

FIGS. 2 and 3 each a cross-sectional fragment with different hinge designs,

FIG. 4 a perspective view of a film dressing in which the supporting sheet is larger than the polymer film, and FIG. 5 a top view on the protecting layer side of a film dressing with round contour FIG. 1 shows in perspective view the construction of a film dressing according to the invention. The flexible, conformable polymer film 2 is covered on the side facing away from the skin by the supporting sheet 1 of the same size. A pressure sensitive adhesive layer 3 is disposed on the side of the polymer film 2 facing the skin and is provided with a two-part protecting layer 4, both parts being equipped by projecting parts of the area with grasping aids 5. A longitudinally creased strip 6 is placed on each of two opposite edges of the film dressing to form a hinge-like connection between 1 and 4.

Other possibilities for forming the hinge 7 are shown in FIGS. 2 and 3. It is evident from the fragments of cross sections that in FIG. 2 the protecting layer itself forms the hinge material and, after winding round the edge, is fastened on the upper side of the supporting sheet 1. In FIG. 3, the protecting layer 4 and supporting sheet are made of a uniform material and therefore allow the required hinge-like connection between the outer layers of the dressing to be produced by simply folding over the edges.

FIG. 4 demonstrates in a perspective view that the size of the supporting sheet 1 in terms of area can be larger than that of the polymer film 2, whose contour 8 is indicated by dotted lines. This furthermore provides an example of film dressings with rounded contours. The solution for the design of the gripping aids 5 is somewhat different here from that in FIG. 1.

A circular film dressing with layers of almost equal area allows the hinge to be formed by forming straight edge sections on opposite sides, as shown by the top view of the protecting layer side 4 in FIG. 5. The gripping aids are evident as further features. This variant of the invention thus makes it possible, inter alia, to apply without difficulty active substance-containing plasters with an extremely thin and conformable backing film of almost any contour.

What is claimed is:

1. A film dressing for a human or animal body comprising:
   a polymer film that is flexible and conformable for application to skin of the human or animal body and has a first polymer film side which is to face away from the skin and a second polymer film side which is to be applied to the skin;
   a supporting sheet having first and second supporting sheet sides and first and second opposing supporting sheet edges, said first supporting sheet side being detachably bonded to said first polymer film side to extend across said polymer film;
   an adhesive layer disposed on said second polymer film side, said adhesive layer being pressure sensitive;
   a protecting layer including at least first and second protecting layer parts detachably adhered to said second polymer film side which can be pulled off said second polymer film side, said first and second protecting layer parts respectively have first and second hinging connections respectively connected to said first and second opposing supporting sheet edges; and said first and second protecting layer parts each having a manipulation device disposed in a region between said first and second opposing supporting sheet edges.

2. The film dressing of claim 1 wherein said hinging connections are formed by adhesive fastening of a edge strip portions of each of the first and second protecting layer parts to said first and second opposing supporting sheet edges, said edge strip portions being folded over onto respective ones of said first and second opposing supporting sheet edges, wherein said first and second opposing supporting sheet edges extend along said second supporting sheet side of the supporting sheet.

3. The film dressing of claim 1 wherein:

the protecting layer and the supporting sheet are formed of a same flat material sheet which is folded over opposite edges of the polymer film to form said hinging connections; and end portions of the flat material sheet are disposed on the adhesive layer.

4. The film dressing of claim 1 wherein said hinging connections are each formed by a longitudinally creased strip attached to said protecting layer and said supporting sheet.

5. The film dressing of claim 4 wherein the longitudinally creased strip is attached by bonding.

6. The film dressing of claim 4 wherein the longitudinally creased strip is attached by sealing.

7. The film dressing of claim 4 wherein the longitudinally creased strip encloses only a portion of a respective one of two opposing edges of said polymer film.

8. The film dressing of claim 1 wherein said polymer film has a rounded contour.

9. The film dressing of claim 1 wherein said polymer film has smaller dimensions than said supporting sheet.

10. The film dressing of claim 1 wherein said adhesive layer contains active substances.

11. The film dressing of claim 10 wherein material containing said active substance is applied to part of said adhesive layer on a side to face the skin of the human or animal body.

12. The film dressing of claim 1 further comprising liquid-absorbing flat material applied to part of said adhesive layer on a side to face the skin of the human or animal body.

13. The film dressing of claim 1 wherein said supporting sheet, said polymer film, said adhesive layer, and said protecting layer form a composite film structure, and said composite film structure has a rounded contour with exception of said first and second opposing supporting sheet edges whereat said hinging connection are formed straight.

* * * * *